United States Patent
Blaser, IV et al.

(10) Patent No.: US 11,517,368 B2
(45) Date of Patent: Dec. 6, 2022

(54) ELECTROCAUTERY SYSTEMS WITH AUTOMATIC SHUT-OFF

(71) Applicants: George Blaser, IV, Somerset, MA (US); Kevin Blaser, Somerset, MA (US); George Blaser, III, Somerset, MA (US); Thomas Calef, Bridgewater, MA (US)

(72) Inventors: George Blaser, IV, Somerset, MA (US); Kevin Blaser, Somerset, MA (US); George Blaser, III, Somerset, MA (US); Thomas Calef, Bridgewater, MA (US)

(73) Assignee: NERVE SAFE LLC, Fall River, MA (US)

(*) Notice: Subject to any disclaimer, the term of this patent is extended or adjusted under 35 U.S.C. 154(b) by 0 days.

(21) Appl. No.: 17/497,508

(22) Filed: Oct. 8, 2021

(65) Prior Publication Data

US 2022/0110670 A1    Apr. 14, 2022

Related U.S. Application Data

(60) Provisional application No. 63/089,650, filed on Oct. 9, 2020.

(51) Int. Cl.
*A61B 18/12* (2006.01)
*A61B 18/00* (2006.01)

(52) U.S. Cl.
CPC ..... *A61B 18/1233* (2013.01); *A61B 2018/00434* (2013.01); *A61B 2018/00595* (2013.01); *A61B 2018/00708* (2013.01)

(58) Field of Classification Search
CPC ...... A61B 18/1233; A61B 2018/00434; A61B 2018/00595; A61B 2018/00708
See application file for complete search history.

(56) References Cited

U.S. PATENT DOCUMENTS

| | | |
|---|---|---|
| 8,932,312 B2 | 1/2015 | McFarlin et al. |
| 9,084,551 B2 | 7/2015 | Brunnett et al. |

(Continued)

FOREIGN PATENT DOCUMENTS

| | | |
|---|---|---|
| CN | 104116558 A | 10/2014 |
| CN | 107320157 A | 11/2017 |

(Continued)

OTHER PUBLICATIONS

"NIM Nerve Monitoring Systems" Jun. 2018, Retrieved on: Aug. 12, 2020, 7 pages, Retrieved from: https://www.medtronic.com/us-en/healthcare-professionals/products/ear-nose-throat/nerve-monitoring/nim-nerve-monitoring-systems.html.

(Continued)

*Primary Examiner* — Thomas A Giuliani
*Assistant Examiner* — Christine A Dedoulis
(74) *Attorney, Agent, or Firm* — Talem IP Law, LLP

(57) ABSTRACT

A cautery safety controller can include a first input to receive a cautery power signal; a first output coupled to a nerve stimulator system; a second input coupled to receive a nerve detected signal; a zero-crossing detector coupled to receive the cautery power signal via the first input and output a nerve sense enable signal via the first output to the nerve stimulator system in response to detecting a zero crossing of the cautery power signal; and a nerve detection decision unit coupled to receive the nerve detected signal via the second input, generate a stop operation signal, and output the stop operation signal via a second output. A cauterizing pencil can be provided with a tap line for providing the cautery power signal. Alternatively, a cautery pad can be provided with a sense electrode for providing the cautery power signal.

15 Claims, 9 Drawing Sheets

(56) References Cited

U.S. PATENT DOCUMENTS

| | | | |
|---|---|---|---|
| 9,997,988 B2* | 6/2018 | Xu | H02M 1/4258 |
| 10,022,090 B2 | 7/2018 | Whitman | |
| 10,092,741 B2 | 10/2018 | Darian | |
| 10,226,633 B2 | 3/2019 | Toth et al. | |
| 10,470,678 B2 | 11/2019 | Strother et al. | |
| 10,631,912 B2 | 4/2020 | McFarlin et al. | |
| 2008/0103504 A1 | 5/2008 | Schmitz et al. | |
| 2010/0143413 A1 | 6/2010 | Papay | |
| 2015/0238259 A1* | 8/2015 | Albeck | A61B 5/4893 606/12 |
| 2016/0242661 A1 | 8/2016 | Fischell et al. | |
| 2018/0042524 A1* | 2/2018 | Inman | A61B 5/1107 |
| 2018/0249954 A1 | 9/2018 | Freeman et al. | |
| 2019/0142509 A1 | 5/2019 | Harmouche et al. | |
| 2019/0201045 A1* | 7/2019 | Yates | H05K 1/189 |
| 2019/0254736 A1* | 8/2019 | Wham | A61B 18/1233 |
| 2019/0313971 A1 | 10/2019 | Lee | |
| 2019/0350597 A1 | 11/2019 | Akbarian et al. | |

FOREIGN PATENT DOCUMENTS

| | | |
|---|---|---|
| CN | 107361820 A | 11/2017 |
| CN | 107361821 A | 11/2017 |
| KR | 101910643 B1 | 10/2018 |

OTHER PUBLICATIONS

International Search Report and Written Opinion issued in International Application No. PCT/US2021/054227, dated Feb. 8, 2022, 11 pages.

* cited by examiner

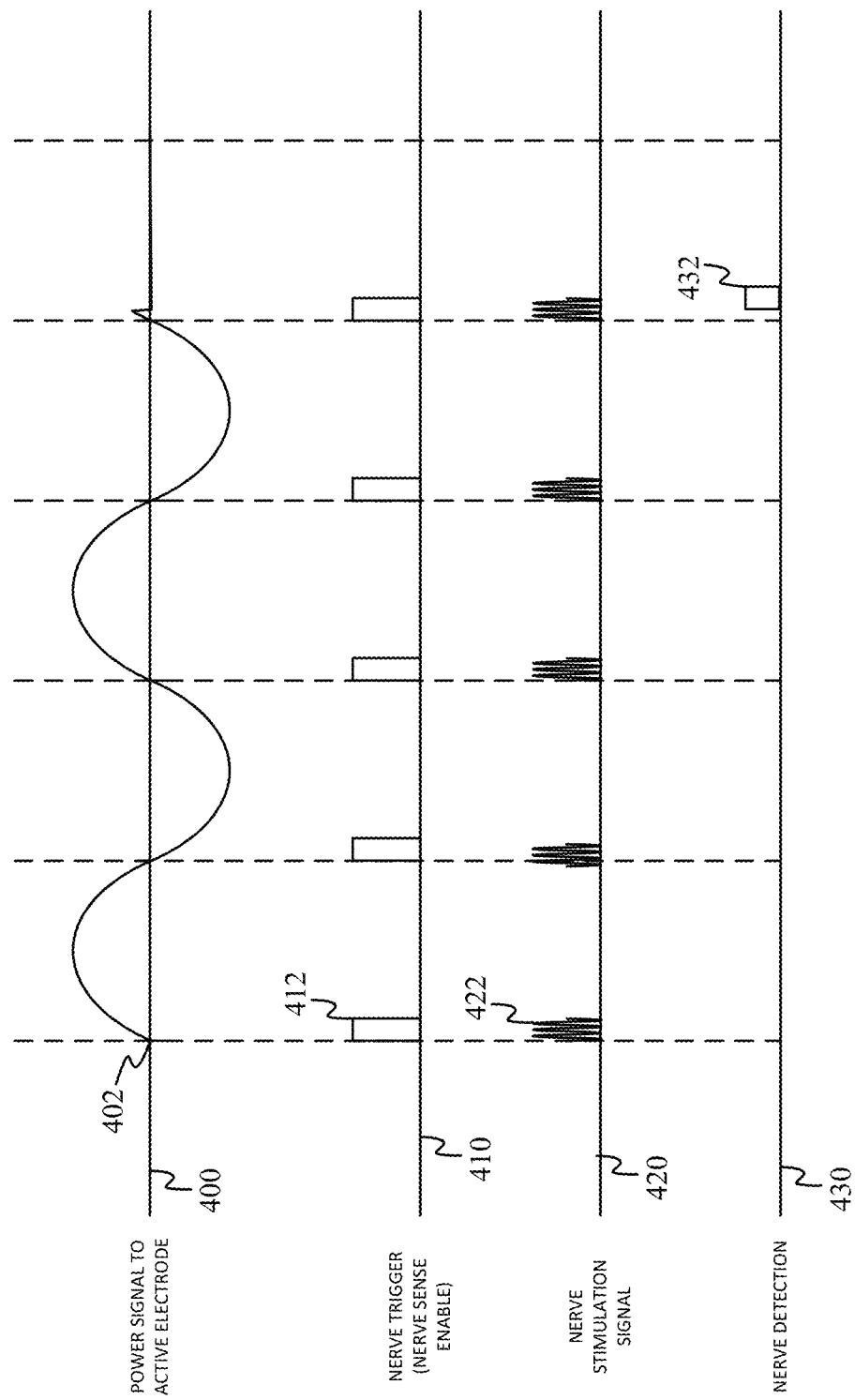

ELECTROCAUTERY SYSTEMS WITH AUTOMATIC SHUT-OFF

CROSS-REFERENCE TO RELATED APPLICATION

This application claims the benefit of U.S. Provisional Patent Application Ser. No. 63/089,650, filed Oct. 9, 2020.

BACKGROUND

Cautery is a medical procedure in which high heat is used on a patient, usually to close off a part of the body to prevent bleeding or infection. In the present day, cauterization techniques are mostly used to close very small wounds, such as small blood vessels, or to excise undesirable growths such as warts and tumors. Electrocautery is a form of cautery that utilizes heat produced by passing an electrical current, usually high-frequency and alternating, through a metal probe to create a very localized area of heating. Electrocautery operation can be monopolar (also referred to as unipolar) or bipolar. Unipolar operation utilizes a single electrode, while bipolar passes current between two electrodes, one coupled to the source and one coupled to ground.

Because the heat of the probe is a function of the waveform passed through the probe, electrocautery is especially advantageous as different waveforms and amplitudes can produce different but specific responses. For example, a continuous waveform can be used to cut tissues while an intermittent waveform can produce a coagulation.

BRIEF SUMMARY

Electrocautery devices and peripherals are described that support automatic shut-off in the presence of a nerve. Electrocautery can be an effective tool for many surgeries despite its inherently invasive nature. One of the greatest dangers in electrocautery is hitting a nerve with the tool, as it is both painful and potentially permanently damaging. The described devices, peripherals, and methods provide a safe surgical operation involving electrocautery.

An electrocautery system with automatic shut-off can include an electrocautery device, a nerve stimulator system, a cautery safety controller, one or more cauterizing pencils, and a cautery pad. A method implemented by the cautery safety controller of an electrocautery system can include detecting a zero crossing of a power signal of the electrocautery device to a cautery pencil. In response to a zero crossing being detected, a nerve stimulation signal can be triggered to be output from the nerve stimulator system. When a nerve detection signal indicating that a nerve has been detected by the nerve stimulator system is received, the operation of the electrocautery device is stopped, for example, by causing the ground path to be disrupted. The cautery safety controller can detect the zero crossing via the cautery pad, the cautery pencil, or directly from the electrocautery device (e.g., at the power supply output to the cautery pencil). In some cases, the electrocautery system further includes a motion detector coupled to the cautery safety controller for confirming that the nerve has been detected.

A cautery safety controller can include a first input to receive a cautery power signal; a first output coupled to a nerve stimulator system; a second input coupled to receive a nerve detected signal; a zero-crossing detector coupled to receive the cautery power signal via the first input and output a nerve sense enable signal via the first output to the nerve stimulator system in response to detecting a zero crossing of the cautery power signal; and a nerve detection decision unit coupled to receive the nerve detected signal via the second input, generate a stop operation signal, and output the stop operation signal via a second output. In some cases, the cautery safety controller can include a third input coupled to receive a secondary nerve detected signal.

A cauterizing pencil can include an active electrode with active conductive line for coupling to a power supply; a contact tip coupled to the active electrode; and a sense electrode with sense conductive line for coupling to a nerve detection circuit, wherein the sense electrode is coupled to the contact tip. In some cases, the cauterizing pencil further includes a tap line coupled to the active conductive line for coupling to a cautery safety controller so that the cautery safety controller can detect a zero crossing of the cautery power signal.

A cautery pad can include a substrate, a return electrode on the substrate, and a cautery sensing electrode on the substrate for coupling to a cautery safety controller so that the cautery safety controller can detect a zero crossing of the cautery power signal.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 4 illustrates an example timing diagram.

DETAILED DESCRIPTION

Electrocautery can be an effective tool for many surgeries despite its inherently invasive nature. One of the greatest dangers in electrocautery is hitting a nerve with the tool, as it is both painful and potentially permanently damaging. To offset this danger, tools and methodologies can be designed to detect nerves in real-time during a surgical operation involving electrocautery, even so far as using the cauterizing pencil itself as a detector to minimize both errors and time spent checking for nerves.

Figure 1:
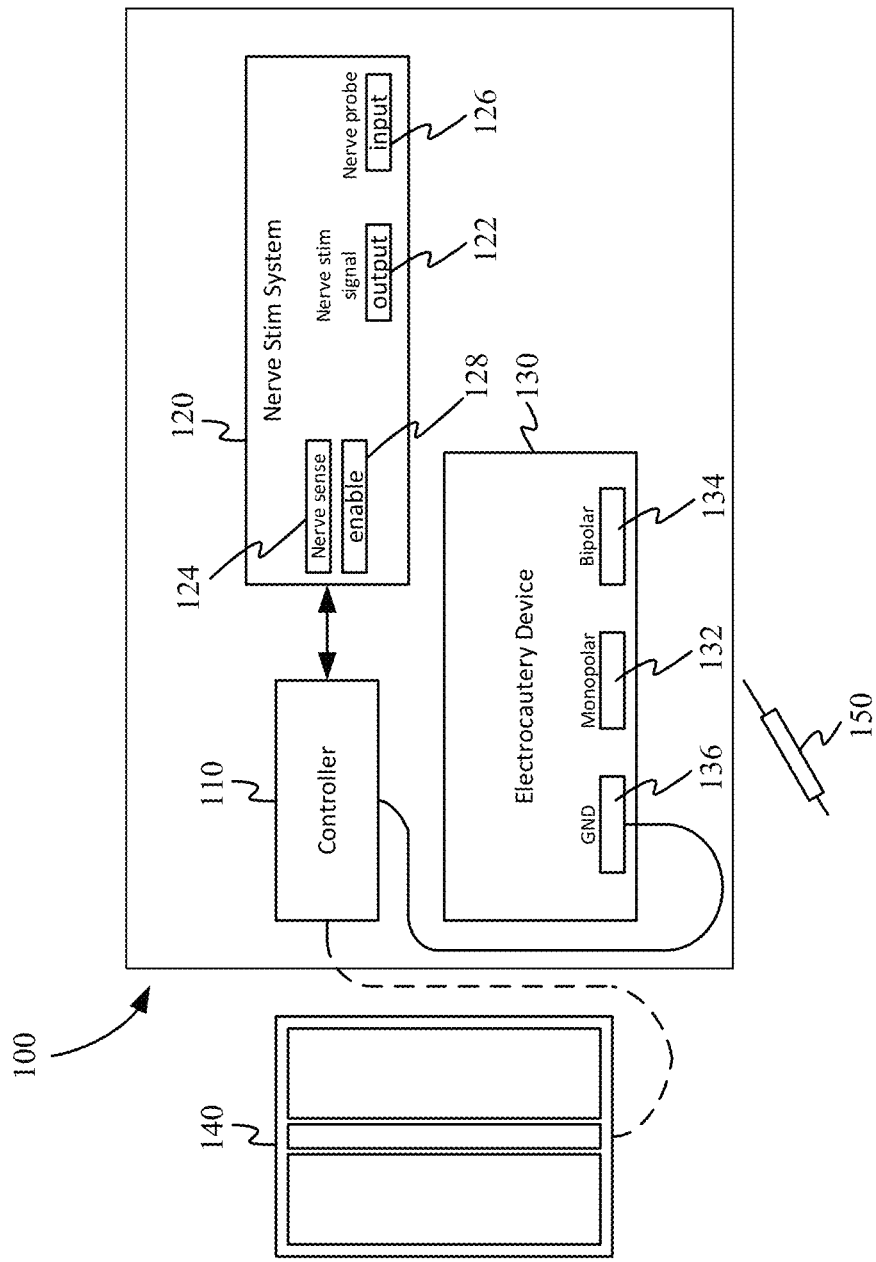
FIG. 1 shows a schematic representation of a system for electrocautery with automatic shut-off.

FIG. 1 shows a schematic representation of a system for electrocautery with automatic shut-off. The system 100 can include cautery safety controller 110, a nerve stimulator system 120, and an electrocautery device 130. System 100 further includes peripherals of a pad 140 and a pencil 150 for performing electrocautery on a patient.

The nerve stimulator system 120 can include outputs of a nerve stimulation signal 122 and a nerve detected signal 124 and inputs of a nerve probe coupler 126 and enable 128. The nerve stimulation signal 122 sends a signal to an output probe coupled to the nerve stimulator system 120. The nerve probe coupler 126 receives a signal indicating a response to the nerve stimulation signal (e.g., which is used to determine whether a nerve has been encountered). The nerve detected signal 124 sends a signal indicating that a nerve has been detected. The enable 128 causes the nerve stimulator system 120 to operate (and send a nerve stimulation signal).

The electrocautery device 130 can include a monopolar output 132, a bipolar output 134, and a ground connection 136 (used for monopolar operation). In monopolar operation, a pencil, such as pencil 150, is used to apply a power signal to cauterize of otherwise affect a material in contact with the pencil tip. In addition, a pad, such as pad 140 is placed on a patient to provide a ground path back to the electrocautery device 130.

Figure 2A:
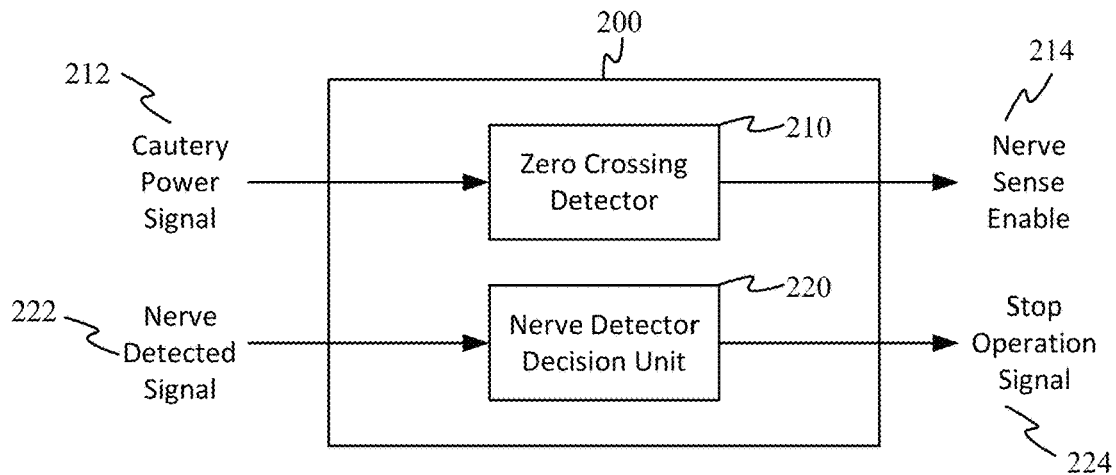
FIGS. 2A-2C illustrate a cautery safety controller and example circuitry.

The cautery safety controller 110 can be coupled to the nerve stimulator system 120, the electrocautery device 130, and, in some cases, the pad 140. The cautery safety controller 110 can perform automatic turn-off of the electrocautery device 130 in order to avoid damage to nerves. The automatic turn-off may be accomplished through inclusion of a power switch controlled by the cautery safety controller 110 or a ground break switch controlled by the cautery safety controller 110. The cautery safety controller 110 can be implemented such as shown in FIG. 2A (or FIG. 8A) and operate such as described with respect to FIG. 3. That is, the cautery safety controller 110 can detect a zero crossing of a power signal from the electrocautery device 130 to a cautery pencil 150, trigger a nerve stimulation signal from the nerve stimulator system 120 in response to the zero crossing, and responsive to receiving a nerve detection signal from the nerve stimulator system 120, cause the electrocautery device 130 to stop operation.

Figure 2B:
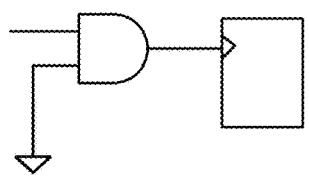
Figure 2C:
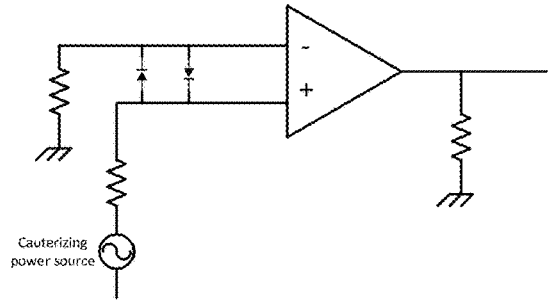

FIG. 2A illustrates a cautery safety controller; FIG. 2B shows an example circuit of a nerve detector decision unit; and FIG. 2C shows an example zero-crossing detector. Referring to FIG. 2A, a cautery safety controller 200 can include at least two input ports, at least two output ports, and at least two modules. The at least two input ports can include ports configured to receive a cautery power signal 212 and to receive a nerve detected signal 222. The cautery power signal 212 can represent when a pencil, such as pencil 150 of FIG. 1, is active (i.e., when the electrocautery device is sending a signal). The nerve detected signal 222 is an input representing that a nerve is apparently in the immediate area of contact between the patient and the pencil. The at least two output ports can include ports configured to send a nerve sense enable signal 214 and to send a stop operation signal 224. The nerve sense enable signal 214 can be a signal that initiates a process at the nerve stimulator system to check for a nerve. Indeed, the cautery safety controller 200 includes a first input to receive the cautery power signal 212, a second input coupled to receive a nerve detected signal 222, a first output coupled to a nerve stimulator system, such nerve stimulator system 120 described with respect to FIG. 1, and a second output providing the stop operation signal 224.

In some cases, the cautery safety controller 200 receives the cautery power signal 212 from an electrocautery device such as electrocautery device 130 of FIG. 1. In some cases, the cautery safety controller 200 receives the cautery power signal 212 from a tap line coupled to an active conductive line of a cauterizing pencil such as described with respect to FIG. 5A. In some cases, the cautery safety controller 200 receives the cautery power signal 212 from a cautery pad comprising a cautery sensing electrode such as described with respect to FIG. 6A.

Figure 5B:
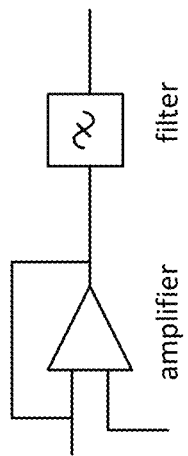
FIG. 5B shows an example conditioning circuit for certain implementations of a cauterizing pencil.
Figure 5A:
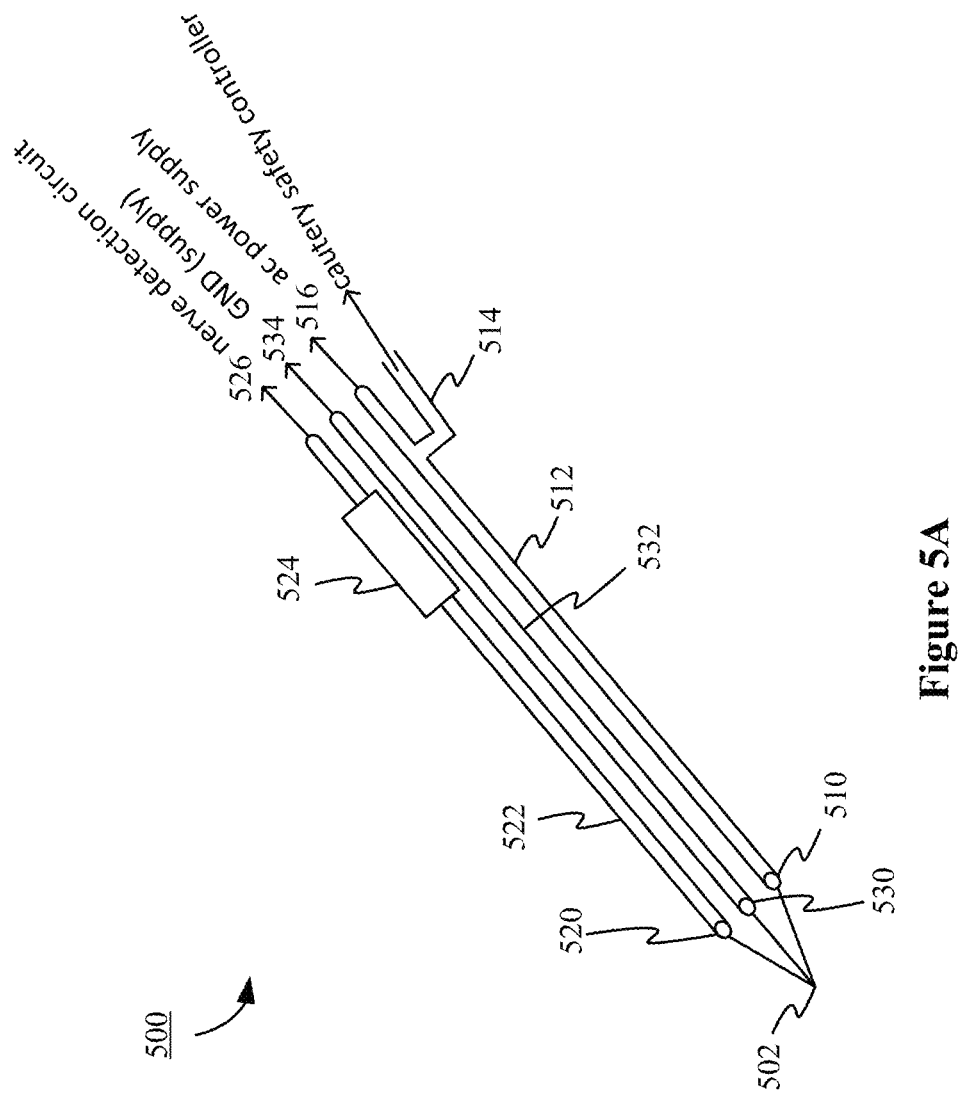
FIG. 5A illustrates features of cauterizing pencils that can be used with an electrocautery device with automatic shut-off.

In some cases, the cautery safety controller 200 receives the nerve detected signal 222 from a sense electrode of a cauterizing pencil such as described with respect to FIG. 5A. In some cases, the cautery safety controller 200 receives the nerve detected signal 222 from the nerve stimulator system, for example, from nerve stimulator system 120 such as described with respect to FIG. 1. In some cases, the cautery safety controller 200 receives the nerve detected signal 222 from a motion sensor such as described with respect to FIG. 7.

Figure 5C:
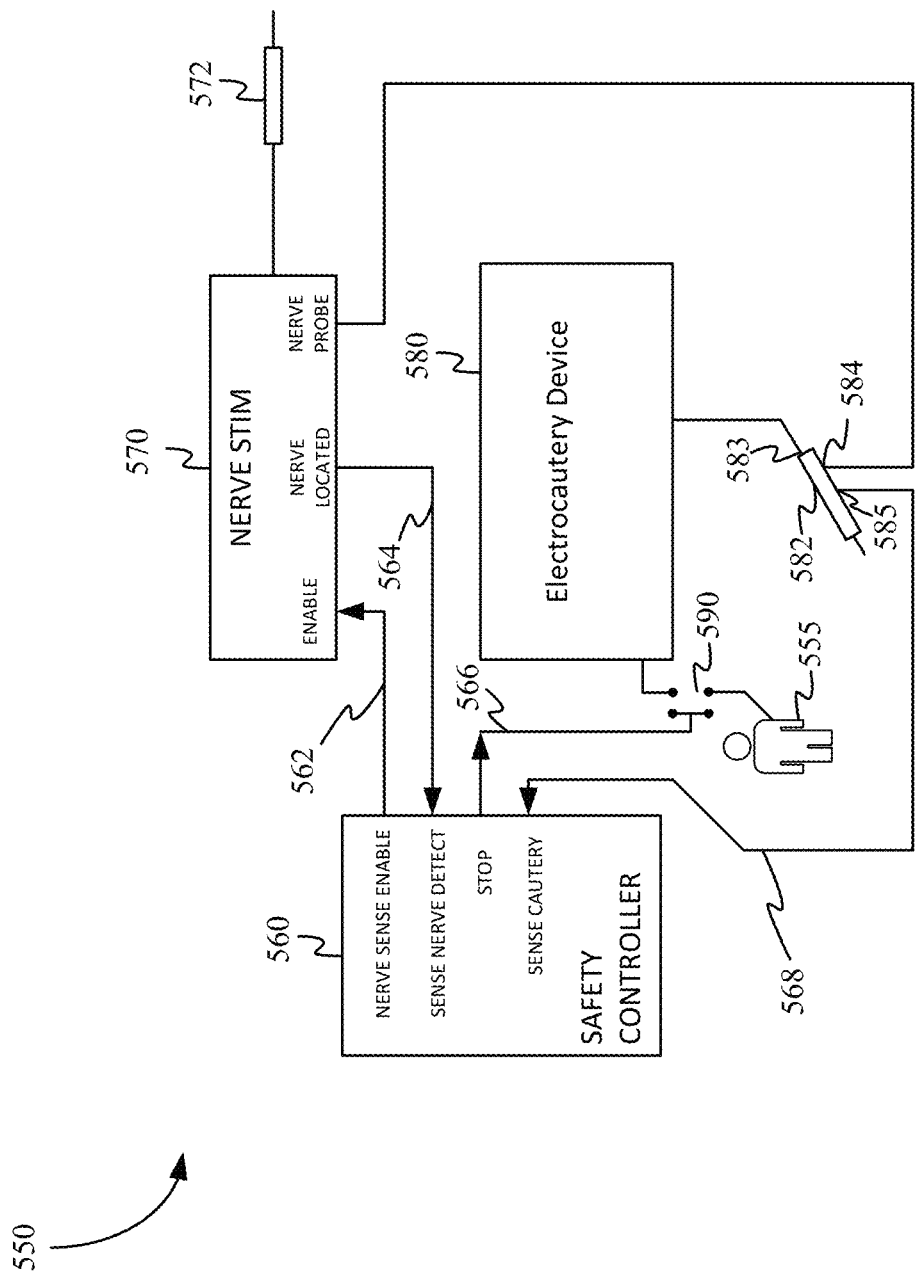
FIG. 5C illustrates an example implementation of a system for electrocautery with a cauterizing pencil having a tap line.
Figure 6A:
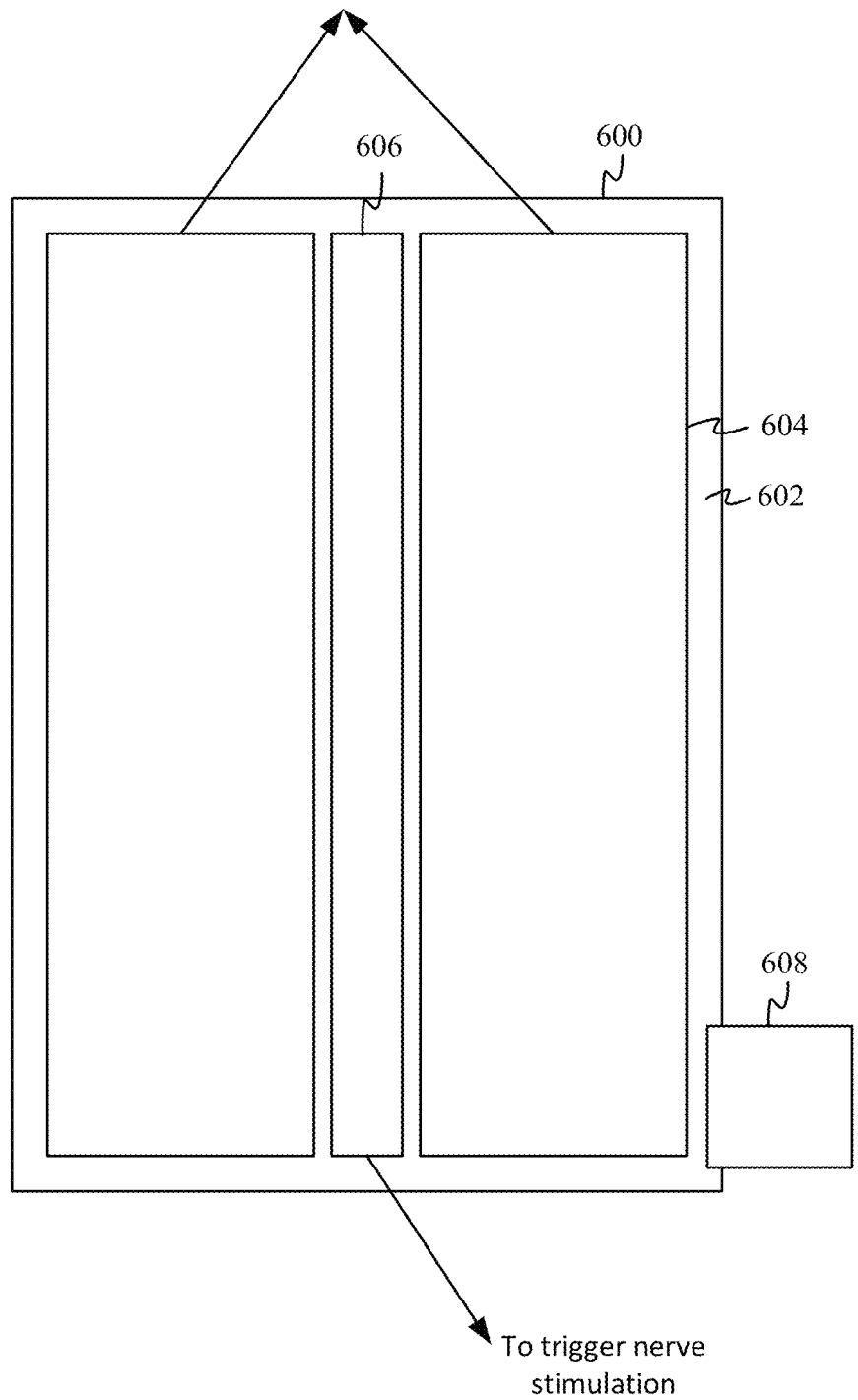
FIG. 6A illustrates a cautery pad that can be used with an electrocautery device with automatic shut-off.
Figure 6B:
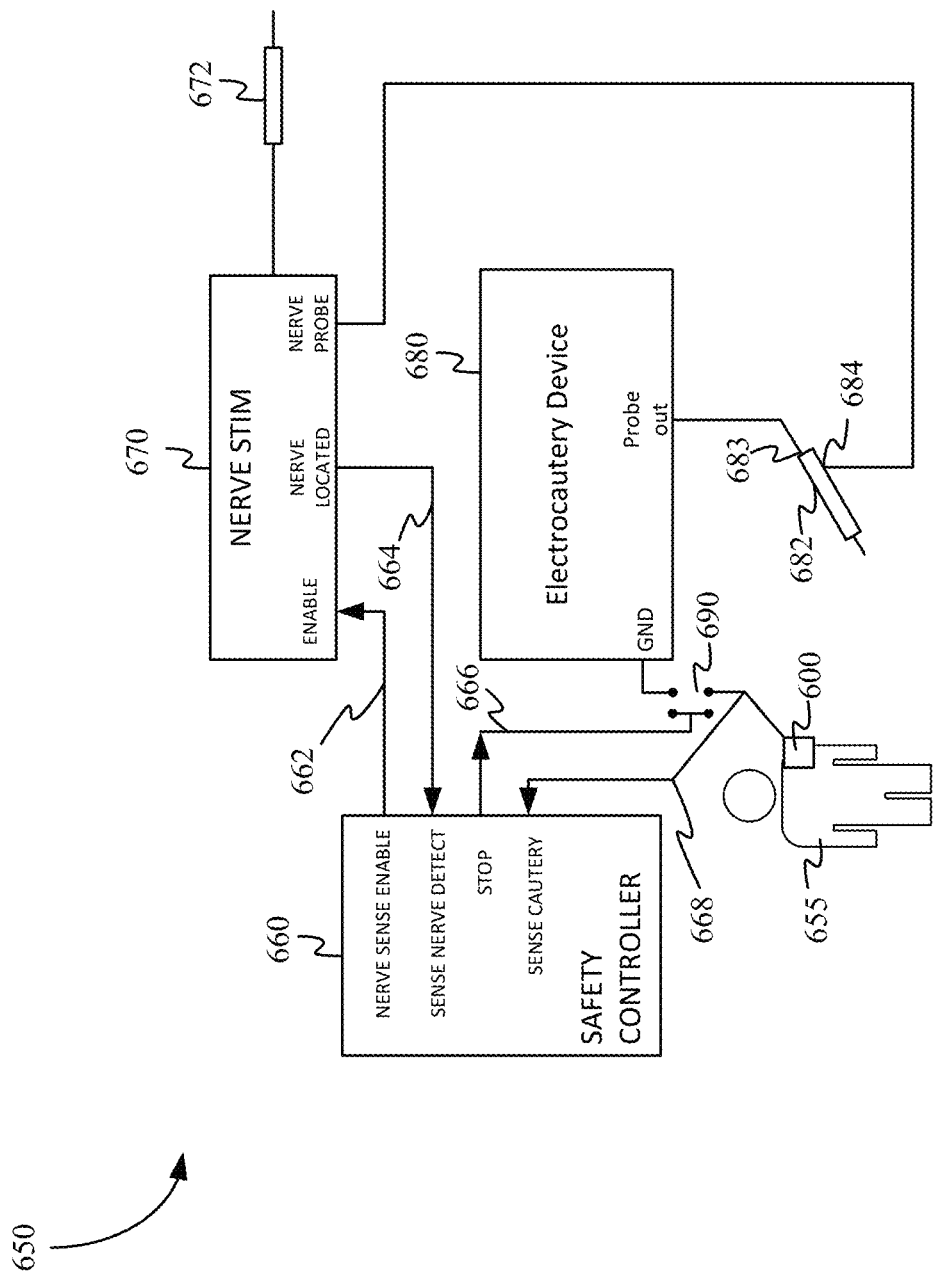
FIG. 6B illustrates an example implementation of a system for electrocautery with a cautery pad having a sensing electrode.

In some cases, such as described in more detail with respect to FIGS. 5C and 6B, the cautery safety controller 200 outputs the stop operation signal 224 to control a switch (not shown). The switch (not shown) disconnects a ground path in response to the stop operation signal 224.

The at least two modules can include a zero-crossing detector 210 and a nerve detection decision unit 220.

The zero-crossing detector 210 can be used to determine when the cautery power signal 212 is temporarily zero. The zero-crossing detector can be coupled to receive the cautery power signal 212 via the corresponding input port and output a nerve sense enable signal 214 via the corresponding output port to the nerve stimulator system in response to detecting a zero crossing of the cautery power signal. The zero-crossing detector 210 can be implemented either digitally or with an analog circuit. If implemented as an analog circuit, the zero-crossing detector 210 can be, for example, an operational amplifier configuration such as illustrated in FIG. 2C. The operational amplifier configuration can include two diodes in opposite directions between the input terminals. The non-inverting terminal can be coupled with the cautery power signal 212, or coupled with a resistor coupled to the cautery power signal 212 and the non-inverting terminal. The inverting terminal can be grounded or coupled with a resistor that is coupled with a ground. The output terminal can be coupled with the nerve sense enable signal 214. The output terminal can be coupled with a resistor that is coupled with a ground.

The nerve detection decision unit 220 can be used to determine whether the nerve detected signal 222 indicates that a nerve was detected. The nerve detection decision unit 220 can be coupled to receive the nerve detected signal 222 via the one of the at least two input ports, generate a stop operation signal 224, and output the stop operation signal 224 via the one of the at least two output ports. The nerve detection decision unit 220 can be implemented either digitally or with an analog circuit. FIG. 2B illustrates a simple implementation of the nerve detection decision unit 220 and can include, for example, a logical AND gate and a latch. The logical AND gate can be coupled to a reference voltage and the nerve detected signal 222. The output of the logical AND gate can be coupled with the input of the latch. The output of the latch may be the stop operation signal 224.

In some cases, the cautery safety controller is implemented using a field programmable gate array (FPGA).

In various implementations, the cautery safety controller can be disposed in or coupled to a pencil, disposed in or coupled to a pad, integrated with the electrocautery device, integrated with a nerve stimulator system, or a separate/independent component that couples to the various other components.

Figure 3:
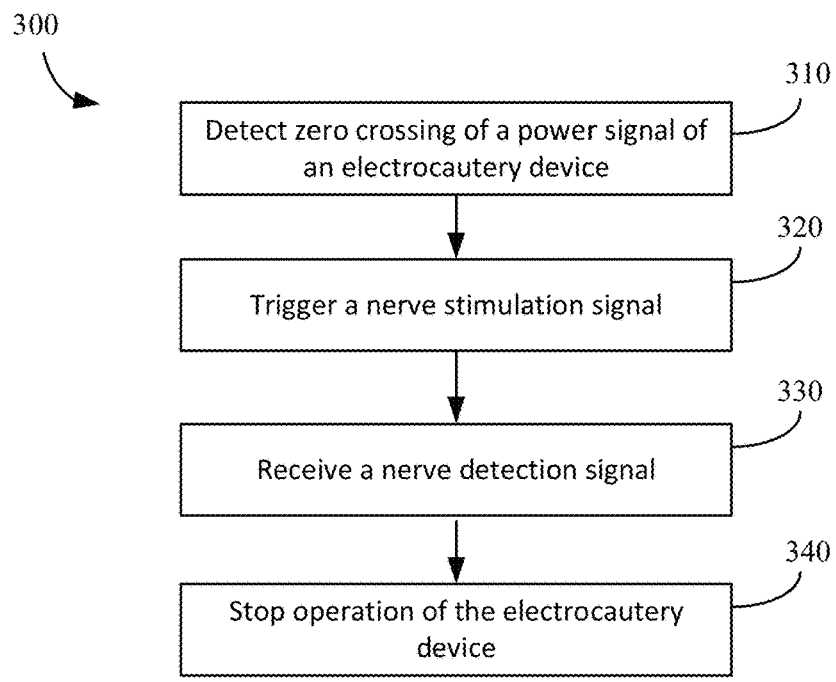
FIG. 3 illustrates a method of controlling an electrocautery device.

FIG. 3 illustrates a method of controlling an electrocautery device; and FIG. 4 illustrates an example timing diagram. Several signals can be seen in the timing diagram of FIG. 4: a power signal 400, a nerve sense enable signal 410 including one or more nerve trigger pulses 412, a nerve stimulation signal 420 including one or more nerve stimulation signal waves 422, and a nerve detection signal 430, with a response indicating that a nerve has been encountered represented in the diagram by a nerve detection pulse 432.

Referring to FIGS. 3 and 4, a method 300 of controlling an electrocautery device can include detecting (310) a zero crossing of a power signal to a cautery pencil. A zero crossing occurs as the power signal swings from a first rail to a second rail and back again. As seen in FIG. 4, a dotted line represents whenever a zero crossing 402 occurs and is detected. The zero crossing 402 can be detected by an analog circuit as described in FIG. 2C. As described with respect to FIG. 2A, the power signal 400 can be received/sensed from different sources depending on implementation. It should be noted that the power signal 400 depicted is sinusoidal in nature, but the power signal 400 can take the form of other waveforms, including discontinuous sinusoids and triangle waves, among others.

The method 300 can further include triggering (320) a nerve stimulation signal in response to the zero crossing. The nerve stimulation signal can be triggered by the cautery safety controller sending a nerve sense enable signal 410 (e.g., as nerve trigger pulse 412) to a nerve stimulator system, which then outputs a nerve probe signal of the nerve stimulation signal waves 422. The length (of time) of the nerve stimulation signal waves 422 (having an appropriate frequency) can vary—in some implementations, the length of the nerve stimulation signal waves 422 can be based on the pulse width of the nerve trigger pulse 412, which itself may be based on the frequency of the power supply signal (and length of time the power supply signal is at or near the zero crossing). The length (of time) can also be fixed manually or automatically by the nerve stimulator system (which may be based on the frequency of the power supply signal and length of time the power supply signal is at or near the zero crossing). The nerve stimulation signal waves 422 can be applied to the patient in a particular area, such as at a spinal area of the patient or other suitable area to couple to nerves in the patient.

Until a nerve detection signal is received, the system continues to perform operations 310 and 320. At some point, a nerve detection pulse 432 may be received after a nerve stimulation signal is applied to the patient, indicating that a nerve is nearby. At this point, the system can automatically stop operation at the electrocautery device. That is, when the nerve detection signal is received (330), the method 300 continues by causing the electrocautery device to stop operation (340). Causing the electrocautery device to stop can be performed in a variety of ways, depending on implementation. A ground path of the electrocautery signal can be disconnected. For example, as described with respect to FIGS. 2A and 2B, a signal can be sent to a switch between ground and the electrocautery device.

FIG. 5A illustrates features of cauterizing pencils that can be used with an electrocautery device with automatic shut-off; and FIG. 5B shows an example conditioning circuit for certain implementations of a cauterizing pencil. The cauterizing pencil 500 can include a contact tip 502, an active electrode 510 coupled to the contact tip 502, and a sense electrode 520 coupled to the contact tip 502.

The active electrode 510 can be coupled to an active conductive line 512 for coupling to the power supply 516. The active electrode 510 can supply the power from a power supply 516 of an electrocautery device, when the pencil is coupled to the electrocautery device via the active conductive line 512, to perform an electrocautery operation.

The sense electrode 520 can be used to receive a response to a nerve stimulation signal applied to a patient if a nerve is present and, in this way, detect if a nerve is touching or about to touch the contact tip 502. The sense electrode 520 can be coupled to a sense conductive line 522 for coupling to a nerve detection circuit 526.

In some cases, the cauterizing pencil can include a tap line 514 coupled to the active conductive line 512 for coupling to a cautery safety controller. An example system using such a pencil is shown in FIG. 5C.

The cauterizing pencil 500 can also optionally include a return electrode 530 coupled to the contact tip 502. The return electrode 530 can allow for bipolar electrosurgery. The return electrode 530 can be coupled with a return conductive line 532, which is itself coupled to ground 534, either immediately or at a supply as part of the electrocautery device.

In some cases, the cauterizing pencil can further include conditioning circuitry 524 coupled to the sense electrode 520 via the sense conductive line 522. As illustrated in FIG. 5B, the conditioning circuitry 524 can comprise an amplifier and filter.

In some cases, a selection circuit (not shown) can be included to enable the sense electrode 520 to be selectively coupled and decoupled with the contact tip 502.

FIG. 5C illustrates an example implementation of a system for electrocautery with a cauterizing pencil having a tap line. Referring to FIG. 5C, a system 550 can include cautery safety controller 560, which may be implemented such as described with respect to FIG. 2A, a nerve stimulator system 570, an electrocautery device 580, and cauterizing pencil 582 having a tap line 585.

In addition to the tap line 585, the pencil 582 for the electrocautery device 580 includes an active electrode with active conductive line 583 for coupling to a power supply of the electrocautery device 580; a sense electrode with sense conductive line 584 for coupling to the nerve stimulator system 570; and a contact tip, coupled to the active electrode and the sense electrode, for contacting a patient 555.

The nerve stimulator system 570 includes a nerve probe output pen 572 for coupling to the patient 555 and receives the nerve signal via the pencil 582. The nerve stimulator system 570 provides a nerve detected signal 564 to the cautery safety controller 560 and receives a nerve sense enable signal 562 from the cautery safety controller 560.

In this implementation, the cautery safety controller receives the cautery power signal 568 from the cauterizing pencil 582. When the cautery safety controller 560 determines that the electrocautery device 580 is to be stopped/turned off, the cautery safety controller 560 sends a stop operation signal 566 to break the ground path, for example, via switch 590.

FIG. 6A illustrates a cautery pad that can be used with an electrocautery device with automatic shut-off. The cautery pad 600 can include a substrate 602, a return electrode 604 on the substrate 602, and a cautery sensing electrode 606 on the substrate 602 for coupling to a cautery safety controller.

The cautery pad 600 can also optionally include a break switch circuit 608 for selectively disconnecting the return electrode 604 from a body in response to a signal from the cautery safety controller. The return electrode 604 may be formed of two conductive pads.

FIG. 6B illustrates an example implementation of a system for electrocautery with a cautery pad having a sensing electrode. System 650 can include cautery safety controller 660, which may be implemented such as described with respect to FIG. 2A, a nerve stimulator system 670, and an electrocautery device 680, and the cautery pad 600.

Here, the pencil 682 for the electrocautery device 680 includes an active electrode with active conductive line 683 for coupling to a power supply of the electrocautery device 680; a sense electrode with sense conductive line 684 for coupling to the nerve stimulator system 670; and a contact tip, coupled to the active electrode and the sense electrode, for contacting a patient 655.

The nerve stimulator system 670 includes a nerve probe output pen 672 for coupling to the patient 655 and receives the nerve signal via the pencil 682. The nerve stimulator system 670 provides a nerve detected signal 664 to the cautery safety controller 660 and receives a nerve sense enable signal 662 from the cautery safety controller 660.

In this implementation, the cautery safety controller receives the cautery power signal 668 from the cautery pad 600 (which senses the signal as part of the ground path). When the cautery safety controller 660 determines that the electrocautery device 680 is to be stopped/turned off, the cautery safety controller 660 sends a stop operation signal 666 to break the ground path, for example, via switch 690.

Figure 7:
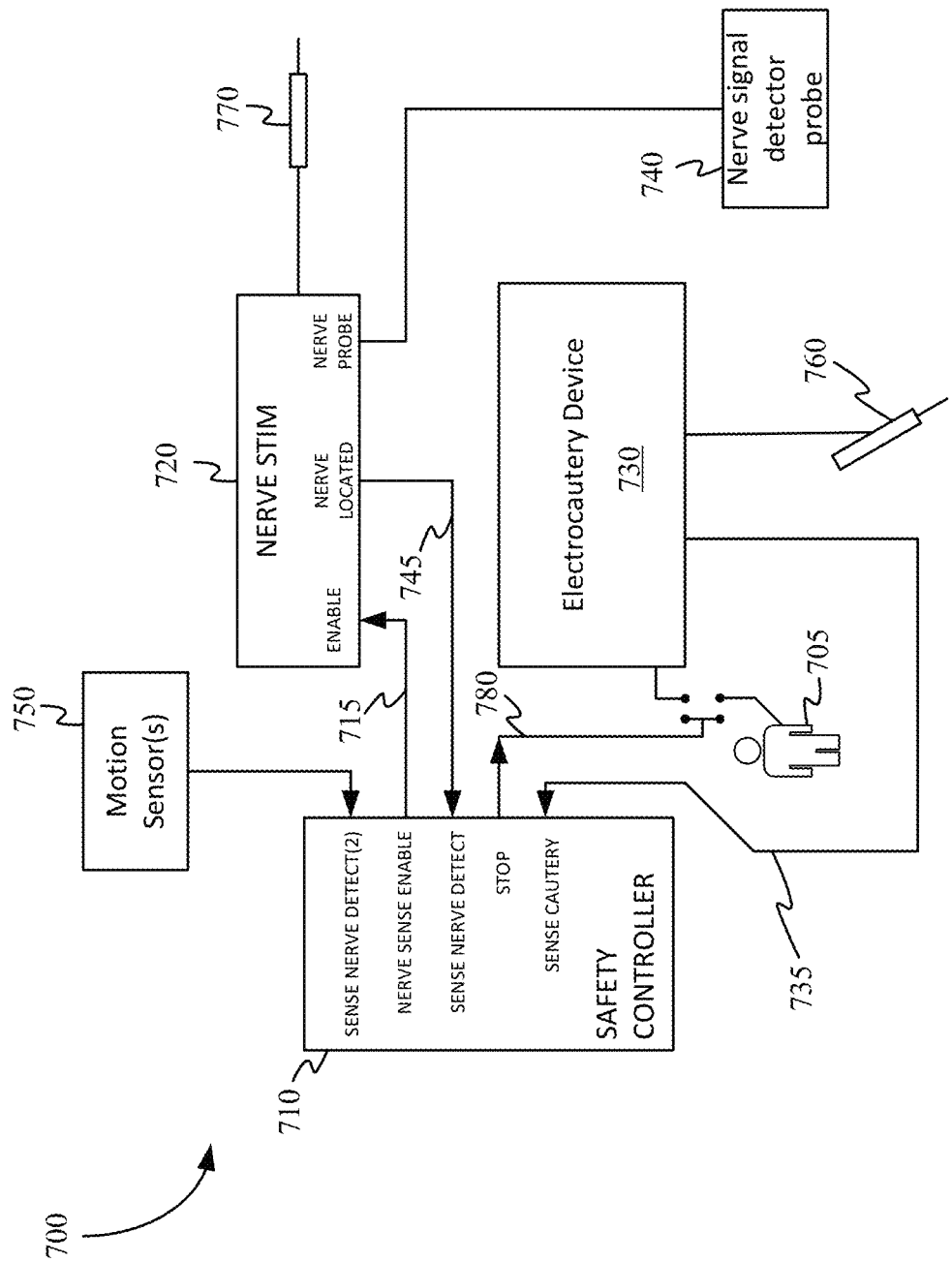
FIG. 7 illustrates an example implementation of a system for electrocautery with a motion sensor.

FIG. 7 illustrates an example implementation of a system for electrocautery with a motion sensor. Referring to FIG. 7, system 700 can include a cautery safety controller 710, a nerve stimulator system 720, and an electrocautery device 730.

It is possible that the signal captured by a lead or other signal detector component 740 of the nerve stimulation system 720 may be noisy or may be too sensitive such that other signals (e.g., from the cautery) are picked up. A motion detector sensor 750 can be included to confirm that the signal captured by the nerve stimulation system 720 from the nerve signal detector probe 740 and sent as nerve detected signal 745 to the cautery safety controller 710 represents a detected signal. That is, the motion sensor 750 can be used to confirm that the received signal is indicative of a response by the nerve (e.g., resulting in motion of the body).

The motion sensor 750 can be any suitable sensor for detecting movement of the body. For example, the motion sensor 750 may be a pressure sensor, vibration sensor, an active electronic motion detector (e.g., optical, microwave, acoustic-based sensor and transmitter), a passive electronic motion detector (e.g., detecting emission or reflection for example using a passive infrared sensor), or even a video camera coupled to a processing system executing software for motion detection.

The motion sensor 750 can be used to decouple motion movement of the body due to the electrocautery device 730 and the nerve stimulator 720. For example, during a cauterizing operation (e.g., applied by pencil 760), localized motion occurs in the muscle of a patient 705. The nerve stimulator signal (e.g., applied by probe 770) can also cause a localized motion. Since the zero crossing of the signal 735 powering the electrocautery device 730 is when the nerve stimulator signal is applied (e.g., in response to the nerve sense enable signal 715 output by the controller 710), the motion detected by the motion sensor 750 at the time of the zero crossing can indicate that a nerve is detected and this signal, alone or in combination with an electrical sensor signal that a nerve is detected (e.g., via the nerve signal detector probe 740), can be used to trigger the stop operation signal 780.

It should be understood that, similarly to the systems shown in FIGS. 1, 5C, and 6B, while these components are shown separately, two or more of these three components may be integrated into a single package or may be separately packaged. For example, in some cases, the controller 710 receives the electrical signal directly from the nerve signal detector probe 740 (instead of via a nerve stimulator system) such that the controller 710 determines whether the electrical signal is indicative of a nerve responding to the nerve stimulation signal. In such a case aspects of nerve stimulation system 720 can be considered to be incorporated in the safety controller package.

Figure 8A:
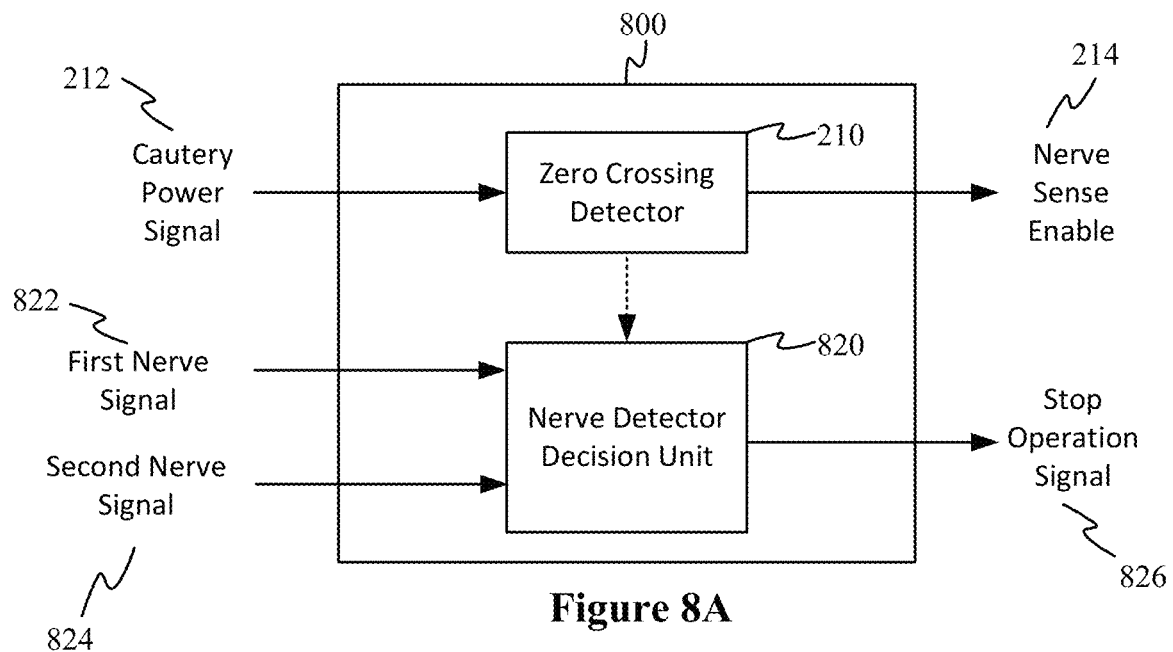
FIGS. 8A-8C illustrate example configurations of a cautery safety controller for a system for electrocautery with a motion sensor.
Figure 8B:
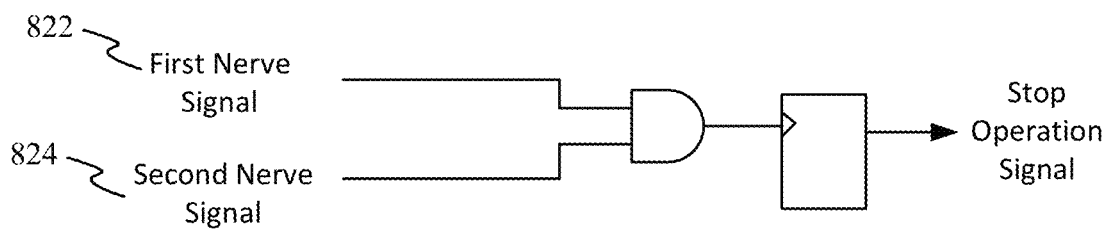
Figure 8C:
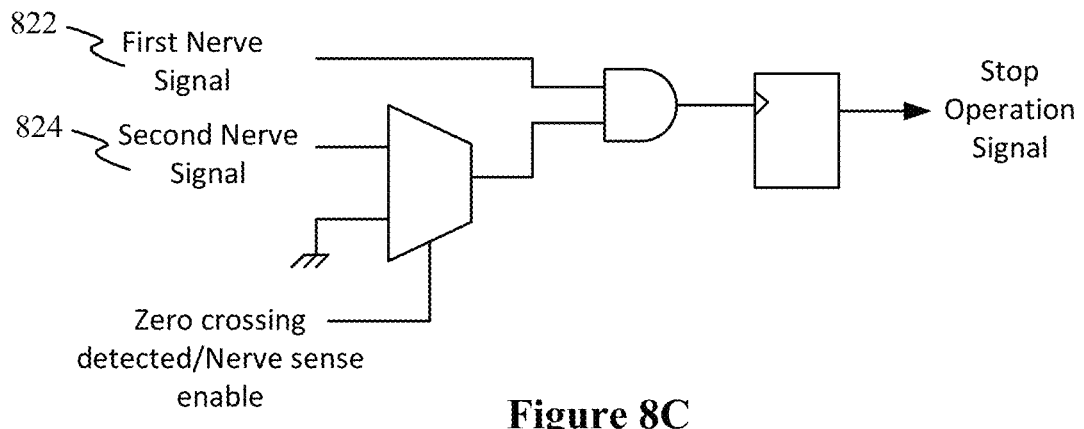

FIGS. 8A-8C illustrate example configurations of a cautery safety controller for a system for electrocautery with a motion sensor; FIG. 8A shows a block diagram of a cautery safety controller; FIGS. 8B and 8C show example circuits for a nerve detector decision unit.

Referring to FIG. 8A, a cautery safety controller 800 can include an input port configured to receive a cautery power signal 212, an output port configured to send a nerve sense enable signal 214, and a zero-crossing detector 210 coupled to receive the cautery power signal 212 via the corresponding input port and output a nerve sense enable signal 214 via the corresponding output port to the nerve stimulator system in response to detecting a zero crossing of the cautery power signal re such as described with respect to the cautery safety controller 200 of FIG. 2A. Different than the cautery safety controller 200, cautery safety controller 800 includes at least two input ports for receiving signals associated with detecting a nerve (e.g., a second input coupled to receive a nerve detected signal and a third input coupled to receive a secondary nerve detected signal from a motion sensor).

In particular, cautery safety controller 800 can include a first nerve sense input port for receiving a first nerve signal 822 (e.g., "nerve detected signal") and a second nerve sense input port for receiving a second nerve signal 824 (e.g., "secondary nerve detected signal"). The first nerve signal 822 can be a signal received from a sense electrode of a cauterizing pencil such as described with respect to FIG. 5A; or a nerve detected signal received from a nerve stimulator system, for example, from nerve stimulator system 120 such as described with respect to FIG. 1. The second nerve signal 824 can be received from a motion sensor 750 such as described with respect to FIG. 7.

The nerve detection decision unit 820 can be used to determine whether a nerve has actually been detected by using the at least two inputs associated with detecting a nerve. In the illustrated example, the nerve detection decision unit 820 is coupled to receive the first nerve signal 822 and the second nerve signal 824 and then generate a stop operation signal 826 to output via an output port in response to both the first nerve signal 822 and the second nerve signal 824 indicating that a nerve is detected. The nerve detection decision unit 820 can be implemented either digitally or with an analog circuit. FIGS. 8B and 8C illustrate two simple circuit implementations of the nerve detection decision unit 820.

Referring to FIG. 8B, a nerve detection decision unit can include, for example, a logical AND gate and a latch. The logical AND gate can be coupled to receive the nerve signal inputs 822, 824. The output of the logical AND gate can be coupled with the input of the latch. The output of the latch may be the stop operation signal 826. Only when both signals agree that a nerve is detected will the stop operation signal be output.

In some cases, one or both of the first nerve signal and the second nerve signal are pre-processed before being input to the AND gate (for the comparison). For example, a second two-input AND gate could be included to receive the first nerve signal and a reference signal (similar to the implementation shown in FIG. 2B); and the output of the second two-input AND gate could be coupled to the logical AND gate at the input coupled to receive the nerve signal input 822. A similar configuration could be used for the second nerve signal (e.g., using an AND gate with one input being the second nerve signal and the other input being a reference signal). In some cases, such as illustrated in FIG. 8C, information of the zero crossing can be used to further confirm that the received signal is from a time frame that a signal regarding a nerve detection.

Referring to FIG. 8C, similar to the implementation shown in FIG. 8B, the nerve detection decision unit includes a logical AND gate and a latch. In the example implementation of FIG. 8C, the zero crossing signal is used to trigger when the second nerve signal is checked. For example, the output of the zero-crossing detector 210 can be used to select between a first state signal (e.g., a ground signal or reference voltage) and the second nerve signal 824. In this manner, if a motion sensor (or other sensor) providing the second nerve signal 824 also picks up motion during a cauterizing event, that signal would not be used by the nerve detector decision unit 820. In some cases, both nerve signals are triggered by the zero crossing signal.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A cautery safety controller comprising:
a zero-crossing detector configured to detect a zero crossing of a cautery power signal of an electrocautery device and output a nerve sense enable signal in response to detecting the zero crossing of the cautery power signal, wherein the cautery safety controller triggers a nerve stimulator system by outputting the nerve sense enable signal to the nerve stimulator system; and
a nerve detection decision unit configured to receive a nerve detected signal, generate a stop operation signal, and output the stop operation signal to cause operation of a cautery device to stop.

2. The cautery safety controller of claim 1, wherein the cautery safety controller receives the cautery power signal from a tap line coupled to an active conductive line of a cauterizing pencil.

3. The cautery safety controller of claim 1, wherein the cautery safety controller receives the cautery power signal from an electrocautery device.

4. The cautery safety controller of claim 1, wherein the cautery safety controller receives the cautery power signal from a cautery pad comprising a cautery sensing electrode.

5. The cautery safety controller of claim 1, wherein the cautery safety controller receives the nerve detected signal from a sense electrode of a cauterizing pencil.

6. The cautery safety controller of claim 1, wherein the cautery safety controller receives the nerve detected signal from the nerve stimulator system.

7. The cautery safety controller of claim 1, wherein the nerve detection decision unit is further configured to receive a secondary nerve detected signal from a motion sensor, wherein the nerve detection decision unit generates the stop operation signal in response to both the nerve detected signal and the secondary nerve detected signal indicating that a nerve is detected.

8. The cautery safety controller of claim 1, wherein the cautery safety controller receives the nerve detected signal from a motion sensor.

9. The cautery safety controller of claim 1, wherein the cautery safety controller outputs the stop operation signal to a switch, the switch disconnecting a ground path in response to the stop operation signal.

10. The cautery safety controller of claim 1, wherein the cautery safety controller is a field programmable gate array (FPGA).

11. An electrocautery system comprising:
an electrocautery device;
a nerve stimulator system;
a cauterizing pencil;
a cautery pad; and
a cautery safety controller, wherein the cautery safety controller comprises:
a zero-crossing detector configured to detect a zero crossing of a cautery power signal of an electrocautery device and output a nerve sense enable signal in response to detecting the zero crossing of the cautery power signal, wherein the cautery safety controller triggers the nerve stimulator system by outputting the nerve sense enable signal to the nerve stimulator system; and
a nerve detection decision unit configured to receive a nerve detected signal, generate a stop operation signal, and output the stop operation signal to cause operation of a cautery device to stop.

12. The electrocautery system of claim 11, wherein the cauterizing pencil comprises:
an active electrode with active conductive line for coupling to a power supply;
a contact tip coupled to the active electrode; and
a sense electrode with sense conductive line for coupling to a nerve detection circuit of the nerve stimulator system, wherein the sense electrode is coupled to the contact tip.

13. The electrocautery system of claim 12, wherein the cauterizing pencil further comprises:
a tap line coupled to the active conductive line for coupling to the cautery safety controller.

14. The electrocautery system of claim 12, wherein the cauterizing pencil further comprises:
a return electrode with return conductive line coupled to the contact tip for bipolar electrosurgery.

15. The electrocautery system of claim 12, wherein the cauterizing pencil further comprises:
a selection circuit selectively coupling the sense electrode to the contact tip.

* * * * *